United States Patent
Haller et al.

(10) Patent No.: US 6,878,135 B1
(45) Date of Patent: Apr. 12, 2005

(54) IMPLANTABLE DRUG INFUSION DEVICE HAVING A FLOW REGULATOR

(75) Inventors: Markus Haller, Begnins (CH); Philippe Renaud, Preverange (CH); Christian Amacker, Eischoll (CH)

(73) Assignee: Medtronic, Inc., Minneapolis, MN (US)

( * ) Notice: Subject to any disclaimer, the term of this patent is extended or adjusted under 35 U.S.C. 154(b) by 464 days.

(21) Appl. No.: 09/712,237

(22) Filed: Nov. 15, 2000

Related U.S. Application Data (63) Continuation of application No. 09/017,194, filed on Feb. 2, 1998, now Pat. No. 6,203,523.

(51) Int. Cl.[7] .................................................. A61M 5/00
(52) U.S. Cl. ....................................................... 604/246
(58) Field of Search .............................. 604/93.01, 131, 604/133, 141, 175, 890.1–891.1, 132, 145, 65–67, 236–238, 246, 247, 256, 151–152, 154; 422/68.1; 204/280; 600/347, 372, 373

(56) References Cited

U.S. PATENT DOCUMENTS

| | | | | |
|---|---|---|---|---|
| 3,731,681 A | | 5/1973 | Blackshear et al. | |
| 4,129,042 A | | 12/1978 | Rosvold | 73/727 |
| 4,428,397 A | * | 1/1984 | Bron | 137/504 |
| 4,596,575 A | | 6/1986 | Rosenberg et al. | |
| 4,666,429 A | | 5/1987 | Stone | |
| 5,101,854 A | * | 4/1992 | Bron | 137/501 |
| 5,163,920 A | * | 11/1992 | Olive | 604/247 |
| 5,171,132 A | | 12/1992 | Miyazaki et al. | 417/413 |
| 5,189,777 A | | 3/1993 | Guckel et al. | 29/424 |
| 5,199,303 A | | 4/1993 | Benedikt et al. | 73/727 |
| 5,271,724 A | | 12/1993 | van Lintel | 417/413 A |
| 5,281,210 A | | 1/1994 | Burke et al. | |
| 5,328,460 A | | 7/1994 | Lord et al. | |
| 5,357,807 A | | 10/1994 | Guckel et al. | 73/721 |
| 5,377,524 A | | 1/1995 | Wise et al. | 73/4 R |
| 5,447,067 A | | 9/1995 | Biebl et al. | 73/514.32 |
| 5,585,011 A | | 12/1996 | Saaski et al. | 216/2 |
| 6,203,523 B1 | | 3/2001 | Haller et al. | |

FOREIGN PATENT DOCUMENTS

FR          1299719      *   6/1961

* cited by examiner

*Primary Examiner*—LoAn H. Thanh
(74) *Attorney, Agent, or Firm*—Keith Campbell; Erik Wald Koetter; Thomas Woods (57) ABSTRACT

An implantable drug infusion device which features an improved flow regulator which permits the flow rate to be independent of reservoir pressure within a given pressure range. The flow regulator features a membrane having a hole, the membrane itself positioned above a bottom layer such that sufficient deflection of the membrane causes the membrane to engage against the bottom layer. As liquid flows through the hole a drag force is applied to the edge of the hole resulting in a deflection of the membrane. Once contact is made between the membrane and the bottom layer, then flow reduced. In a further embodiment the bottom layer features a variable flow channel such that upon membrane deflection flow may only proceed through the hole and through the flow channel. By tailoring the shape and length of the variable flow channel the flow characteristics of the regulator versus pressure may be adjusted. In a further embodiment the flow regulator also features a flow sensor integrated therewith. This integrated sensor provides a measurement of flow and may be coupled to the flow regulator to provide feedback thereto.

10 Claims, 6 Drawing Sheets

IMPLANTABLE DRUG INFUSION DEVICE HAVING A FLOW REGULATOR

RELATED APPLICATIONS

This application is a continuation of Ser. No. 09/017,194 filed Feb. 2, 1998 now U.S. Pat. No. 6,203,523.

This application is related to one or more of the following patent applications, each of which is hereby incorporated herein by reference and assigned to the assignee of the present application:

U.S. patent application Ser. No. 09/017,198 filed Feb. 2, 1998 for "System For Locating Implantable Medical Device" to Markus Haller and Koen Weijand;

U.S. patent application Ser. No. 09/017,195 filed Feb. 2, 1998 for "Implantable Drug Infusion Device Having A Safety Valve" to Markus Haller and Koen Weijand; and U.S. patent application Ser. No. 09/017,196 filed Feb. 2, 1998 for "Implantable Drug Infusion Device Having An Improved Valve" to Markus Haller, T. S. J. Lammerink and Niels Olij.

FIELD OF THE INVENTION

The present invention relates to the field of implantable drug infusion devices and more particularly to an implantable drug infusion device having a flow regulator.

BACKGROUND OF THE INVENTION

Implantable drug infusion devices are used to provide patients with a constant or programmable long term dosage or infusion of a drug or any other therapeutic agent. Essentially such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The Medtronic SynchroMed™ pump further includes an antenna to permit the remote programming of the pump. Needless to say, in view of these various components, the cost as well as the size of active drug infusion devices is greater than desired.

Passive drug infusion devices, in contrast, do not feature a pump, but rather rely upon a pressurized drug reservoir to deliver the drug. Thus such devices tend to be both smaller as well as cheaper as compared to active devices. An example of such a device includes the Medtronic IsoMed™. This device delivers the drug into the patient through the force provided by a pressurized reservoir. In particular, this reservoir is pressurized with a drug to between 20 to 40 psi (1.3 to 2.5 bar) and is used to deliver the drug into the patient's system. Typically the flow path of the drug from the reservoir to the patient includes a flow restrictor, which permits a constant flow rate. The flow rate, however, is only constant, if the pressure difference between reservoir and patient does not change. Factors that could impact this pressure difference include temperature, pressure-volume dependence of reservoir and altitude, among others. The selected pressure for the reservoir is thus typically quite high, so that absolute pressure changes only cause small and acceptable errors in flow rate. This also requires, however, the drug to be injected into the reservoir using still higher pressure. This is often a very difficult to achieve using a hand operated syringe.

In addition such devices present challenges to accurately deliver a precise dosage of drug to the patient. As the amount of drug is removed from the reservoir, the pressure in the reservoir drops. This, in turn, affects the flow rate such that only over a limited pressure range will the flow rate be constant. Still further, because the ambient pressure changes in which the patient exists (due to weather or altitude for example) the resistance to drug infusion likewise changes, further affecting the flow rate. Temperature will also have a similar impact.

Thus there is a need for a drug infusion system which will permit the drug flow rate to be independent of reservoir pressure within a given pressure range.

SUMMARY OF THE INVENTION

The present invention provides an implantable drug infusion device which features an improved flow regulator which permits the flow rate to be independent of reservoir pressure within a given pressure range. The flow regulator features a membrane having a hole, the membrane itself positioned above a bottom layer such that sufficient deflection of the membrane causes the membrane to engage against the bottom layer. As liquid flows through the hole a force is applied to the membrane, resulting in a deflection of the membrane which, in turn, impedes the flow path. In a further embodiment the bottom layer features a variable flow channel such that upon membrane deflection flow may only proceed through the hole and through the flow channel. By tailoring the shape and length of the variable flow channel the flow characteristics of the regulator versus pressure may be adjusted. In a further embodiment the flow regulator also features a flow sensor integrated therewith. This integrated sensor provides a measurement of flow and may be coupled to the flow regulator to provide feedback thereto.

BRIEF DESCRIPTION OF THE DRAWINGS

The FIGS. are not necessarily to scale.

DETAILED DESCRIPTION OF THE DRAWINGS

Figure 1:
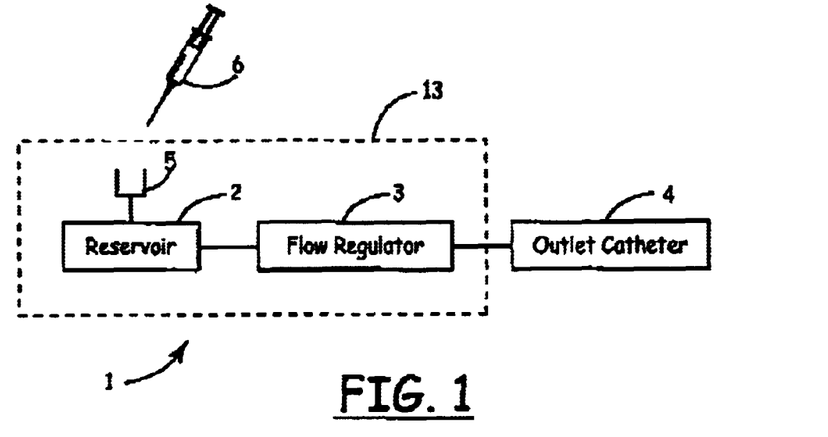
FIG. 1 is a block diagram of an implantable drug infusion device according to the present invention.

FIG. 1 is a block diagram of an implantable drug infusion device and in particular of a passive system to deliver drugs and other therapeutic agents. As seen, such a system 1 comprises a reservoir 2, flow regulator 3 and outlet catheter 4. The reservoir is a pressurizable reservoir to hold drugs and other therapeutic agents. Reservoir may be of a standard design, such as that used in the above mentioned Medtronic IsoMed™ implantable drug infusion system. Flow regulator 3 is coupled to the reservoir and the outlet catheter. Flow regulator controls the flow of material which may be transmitted from the reservoir to the outlet catheter and in particular permits the flow rate to be independent of reservoir pressure within a given pressure range. System may be refilled through injection port 5 through the use of a needle 6 as is well known. Surrounding all components of the implantable pump other than the outlet catheter is a hermetic closure 13 as is well known in the art.

Figure 2:
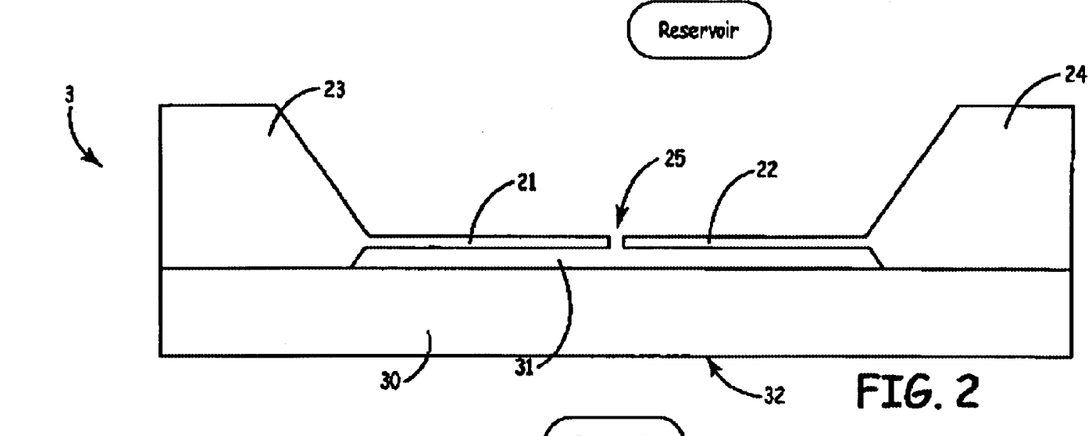
FIG. 2 is a side view of a flow regulator according to the present invention in which the system pressure is low and the regulator membrane is not deflected.

FIG. 2 is a side view of a flow regulator according to the present invention. In this view the reservoir pressure is low. As seen, flow regulator comprises a membrane 21, 22 cantilevered from shoulders 23 and 24 respectively. In the preferred embodiment membrane is circular, although other shapes may also be used, e.g. rectangular.

Center of the membrane features flow lumen 25. The membrane is further disposed above a substrate 30 such that cavity 31 is defined. Substrate 30, in turn, has an outflow tract 32 coupled to cavity 31. Thus, unless activated by pressure, the membrane remains in the position as shown and fluid flows through flow lumen 25 into cavity 31 and thereafter through outflow tract 32. Outflow tract is coupled, in turn, to outlet catheter (although not shown in this view). Outlet catheter may be of any model desired and suited to the patient's requirements. Depending on the amount of pressure exerted by the fluid, the membrane may be either in the position shown or deflected any amount as permitted by substrate 30. In the preferred embodiment shoulders and membrane are silicon and substrate is Pyrex™ glass, although other materials may also be used such as titanium or tantalum. Moreover, the areas of substrate and membranes in contact with any drug or fluid are further preferably coated with diamond or diamond-like carbon so as to inhibit any interactions between the drug or fluid and the materials. Such coatings may be selected according to the particular drug or fluid to be infused.

Figure 3:
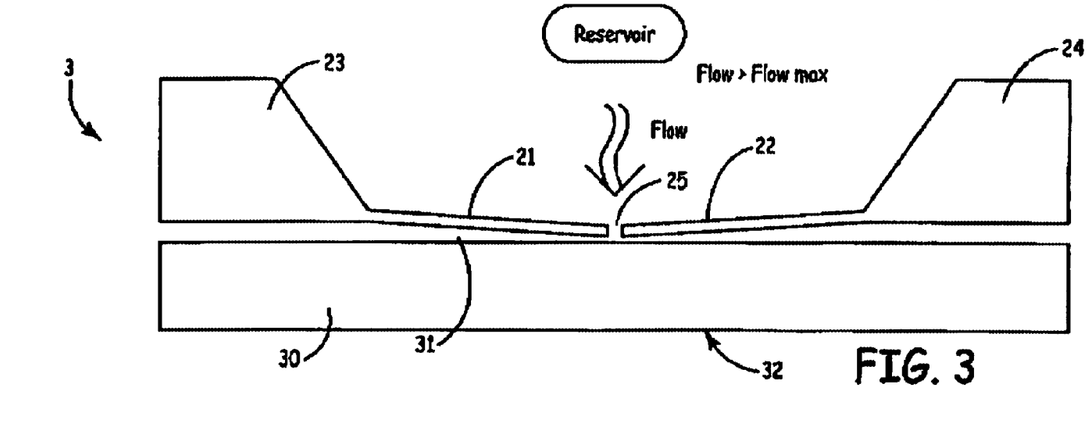
FIG. 3 is a side view of a flow regulator according to the present invention in which the system pressure is high and the membrane is deflected.

FIG. 3 is a side view of a flow regulator according to the present invention in which the system pressure is high. As seen in this embodiment, the pressure of the fluid causes the membrane to be deflected and strike against substrate 30. In such a manner the fluid pathway (flow lumen 25 into cavity 31 and thereafter through outflow tract 32) is blocked by the membrane itself and all fluid flow is thus stopped.

Figure 4:
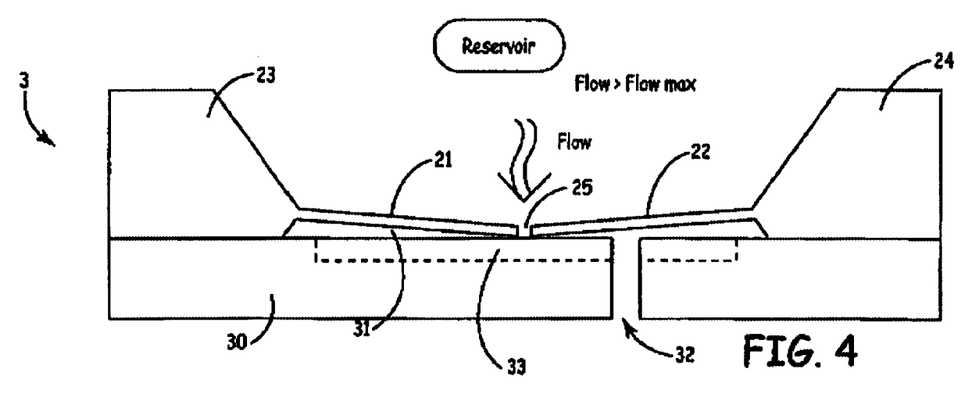
FIG. 4 is a side view of a further embodiment of a flow regulator.

FIG. 4 is an additional embodiment of the present invention and, in particular, the preferred embodiment of flow regulator which features a variable flow restrictor channel 33. As seen in this embodiment, flow regulator features a variable flow restrictor channel which provides a pathway through which flow may continue even though the membrane is disposed against a surface in substrate 30. In particular, flow proceeds through lumen 25 into the variable flow restrictor channel 33 to the outlet 32. Because membrane strikes the top of substrate all flow is forced to go to the "beginning" of the variable flow restrictor channel. As more pressure is applied to the membrane by the fluid, the membrane is deflected to a greater degree, a greater contact area is made between the membrane and the substrate, and the fluid is forced to flow through a longer pathway through the variable flow restrictor channel. In the preferred embodiment the length of the flow channel is directly proportional to the flow resistance. The increase in contact area due to pressure proportionally lengthens the distance in which the fluid flows exclusively within the flow channel. Thus the flow through the restrictor channel is directly proportional to the pressure applied to the fluid within that channel. This capability thus provides this embodiment with the ability to directly compensate pressure inaccuracies as well as pressure variations within any of the system components (upstream of the flow sensor) such as the reservoir, when such pressure anomalies are with the (upstream of the flow sensor) specified pressure region. Ultimately, this design permits the flow rate to be independent of reservoir pressure within a given pressure range.

Figure 5A:
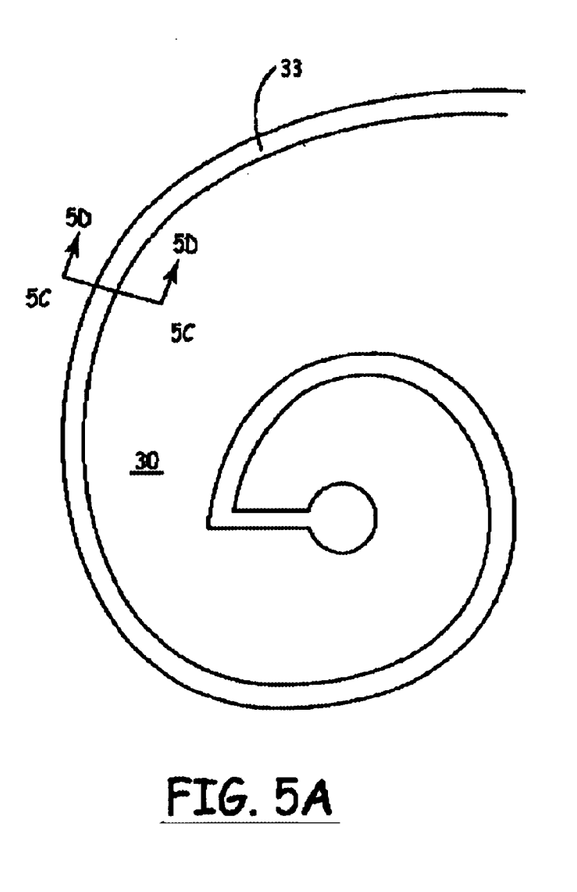
FIG. 5A is a top view of the variable flow restrictor channel used in the embodiment depicted in FIG. 4 of the present invention.
Figure 5B:
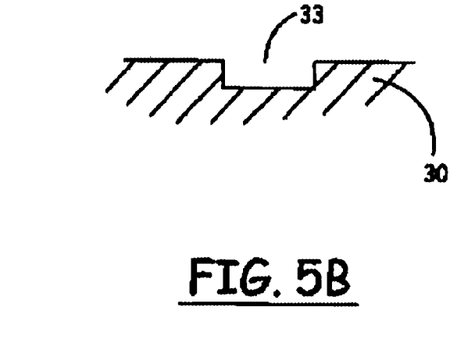
FIG. 5B is a sectional view of the variable flow restrictor shown in FIG. 5A.
Figure 5C:
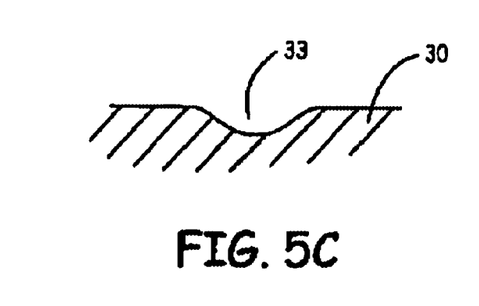
FIG. 5C is a sectional view of an alternative variable flow restrictor channel.

FIG. 5A is a top view of a variable flow restrictor channel used in the preferred embodiment. As seen in this embodiment, restrictor channel is essentially spiral shaped according to the following equation:

$$x = \frac{z \cdot \cos t}{t} \text{ and } y = \frac{a \cdot \sin t}{t} \text{ for } -\infty < t < 0 \text{ and } 0 < t < \infty$$

where "a" is 1 in the preferred embodiment, although any value between approximately 0.1 to 100 may also be chosen FIG. 5B is a sectional view of the flow restrictor channel of FIG. 5A taken along the line 5B—5B. As seen in this embodiment, the restrictor channel is essentially square in shape and has a depth roughly equal to the width. Of course, other cross sectional shapes of restrictor channel may also be used, such as circular, as seen in FIG. 5C or other shapes, triangular, etc. What is important for the flow characteristics of the regulator, however, is the cross sectional area of the channel. In the preferred embodiment the channel has a width of 15 μm and depth of 10 μm which permits a essentially constant flow rate of 500 μm over a pressure range of between approximately 2 to 8 psi above ambient pressure. Moreover, although the cross sectional area and shape of the restrictor channel is constant in the preferred embodiment, either the shape or area or both may be varied along the various portions in order to provide other flow characteristics besides those of the preferred embodiment.

Figure 6:
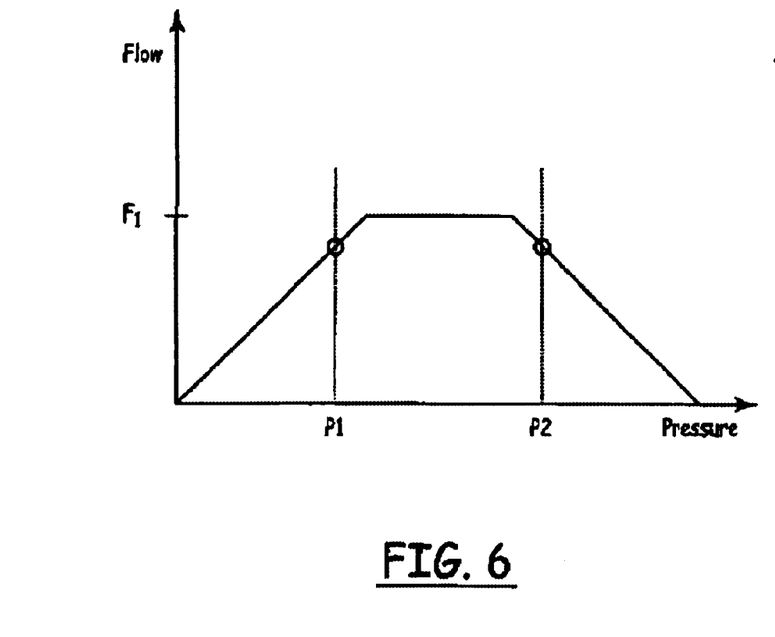
FIG. 6 depicts the flow versus pressure for one embodiment of the present invention showing, in particular, the linear flow between the two pressures which may be permitted using this present invention.

FIG. 6 is a graph showing the flow rate versus pressure of the preferred embodiment. As seen, due to the usage of the deflected leaflets in conjunction with the variable flow restrictor channel the flow rate may be caused to be constant over a pressure range. In this chart P1 is 2 psi, P2 is 8 psi and F1 is 500 ml.

Figure 7:
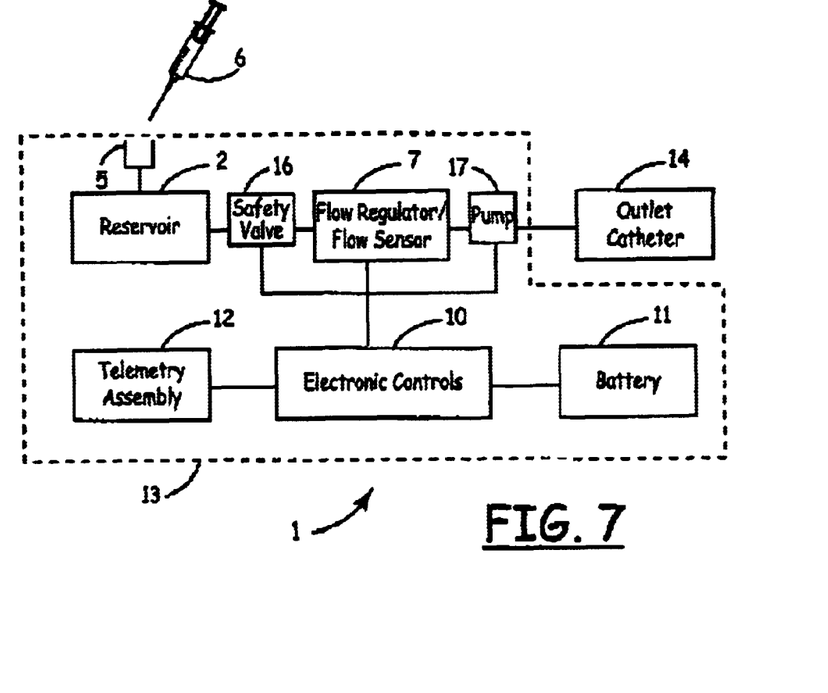
FIG. 7 is a block diagram of an implantable drug infusion device which features an integrated self-test mechanism on the flow regulator.

FIG. 7 is a block diagram of an alternative embodiment of the present invention. As seen, such a system 1 comprises a reservoir 2, flow regulator/flow sensor 7, electronic controls 10, battery 11, telemetry assembly 12 and outlet catheter 4. Flow regulator/flow sensor 7 is coupled to the reservoir across safety valve 16 and further coupled to the outlet catheter across pump 17. Flow regulator/flow sensor regulates the flow of material which may be transmitted from the reservoir to the outlet catheter by pump in a manner to the flow regulator already described above, i.e. it regulates flow such that flow rate is independent of reservoir pressure within a given pressure range. Moreover, in this embodiment, the flow regulator also functions as a flow sensor to permit the flow rate to be sensed such that the device can track how much drug is delivered. Further, this component also permits the device to test itself so as to check and monitor the actual flow rate. As already described above, the system may be refilled through injection port 5 through the use of a needle 6 as is well known. Surrounding all components of the implantable pump other than the outlet catheter is a hermetic closure 13 as is well known in the art. Electronic controls 10, battery 11, telemetry assembly 12 and pump 17 are all constructed in any manner well known in the art. Electronic controls are powered by battery 11 and may receive remote operation instructions via telemetry assembly 12, as is well known in the art. Safety valve is preferably of a design as shown in the co-pending application of Haller et al. "Implantable Infusion Device Having Safety Valve" (P-7356) filed this same day and incorporated herein by reference.

Figure 8:
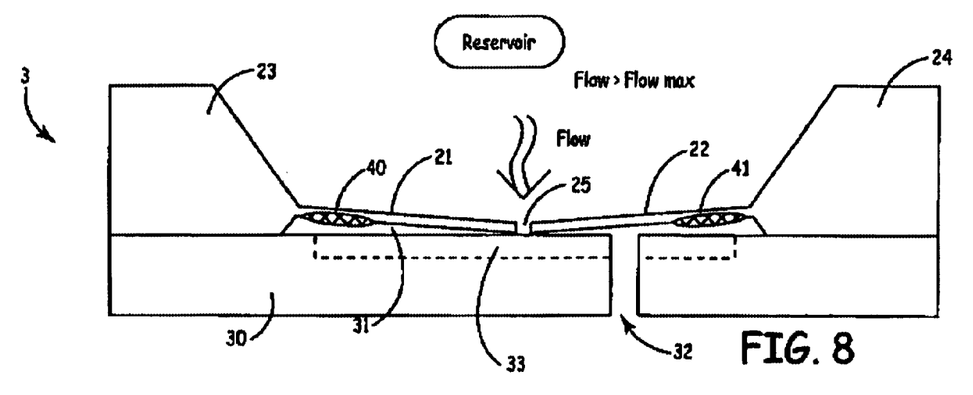
FIG. 8 is a side view of a flow regulator which features an integrated self-test mechanism on the flow regulator.

FIG. 8 is a side view of a flow regulator/flow sensor used in the system of FIG. 7 As seen, this embodiment is essentially the same as that shown in FIG. 4. That is, flow regulator comprises membrane 21 cantilevered from shoulders 23 and 24 respectively disposed above a variable flow restrictor channel within substrate 30. As already discussed above, channel provides a pathway through which flow may continue even though the membrane is disposed against the surface of substrate 30. In the present embodiment, the flow regulator/flow sensor further features one or more piezo-resistive elements 40, 41 integral with the membrane such that deformation or bending of the leaflets is detected by the elements. Such elements are coupled to the electronic controls, which process the signals and extract information as to element deformation and thus flow through the valve. Although piezo-resistive elements are used, other types of elements may also be used, such as capacitive or inductive.

Figure 9:
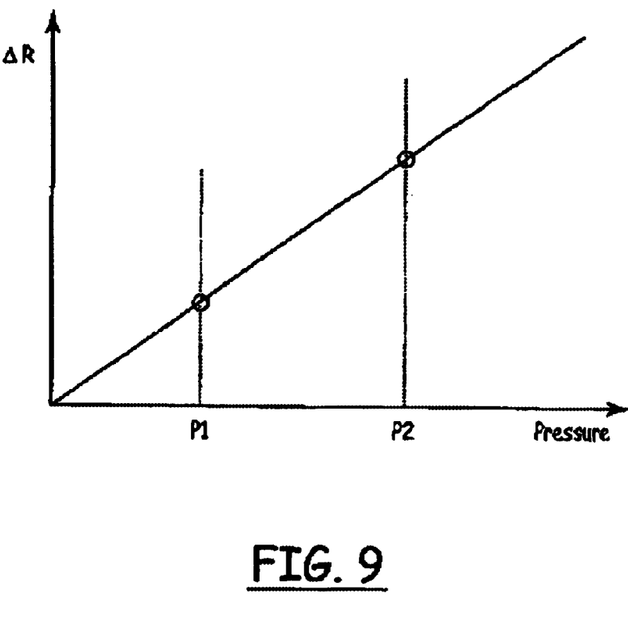
FIG. 9 depicts the change in resistance of the piezo-resistors used in the flow sensors-versus reservoir pressure.

FIG. 9 is a graph showing the change in resistance to flow versus pressure of the preferred embodiment. As seen, due to the usage of the deflected membrane in conjunction with the variable flow restrictor channel the change is resistance to flow increases in proportion to the pressure.

Figure 10:
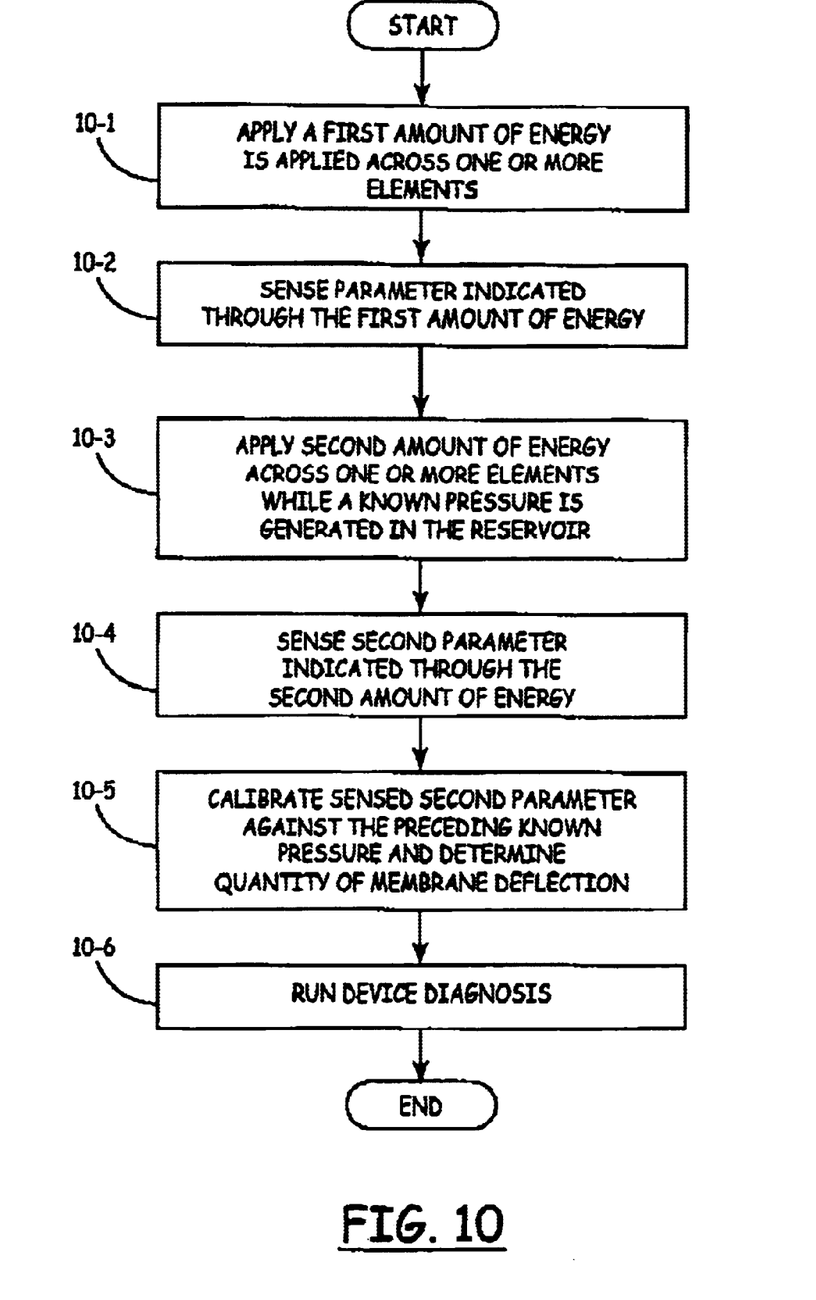
FIG. 10 is a flow chart depicting steps employed in a self-test feature according to one embodiment of the present invention.

FIG. 10 is a flow chart depicting the steps used of a self-test feature made possible through the one or more piezo-resistive elements 40, 41 integral with the membrane. In particular this feature is used to quantify membrane deflection. This is important because, the membranes may, over time, take a set, that is exhibit a permanent deflection. Thus the self test permits the membrane position to be precisely measured. Such information may be then used to assess device operation, e.g. the actual flow rate of fluid through the regulator amount of refill reservoir required by the or device malfunction. Typically this self test procedure is performed at device implant or follow-up by the physician.

As seen in FIG. 10 at 10-1 a first amount of energy is apply across one or more piezo-resistive elements 40, 41. Next at 10-2 a parameter indicated through the first amount of energy is sensed. Such parameters may include resistance, impedance or capacitance, for example. Because in the preferred embodiment the elements are piezo-resistive, then the parameter preferably sensed would be the electrical resistance in the elements. The exact type of parameter is not crucial to the self test feature, nor is it whether the elements are piezo resistive or piezo capacitive, etc. Next at 10-3 a second amount of energy is apply across one or more piezo-resistive elements 40, 41 while a know pressure is generated in the reservoir. Next at 104 a second parameter indicated through the second amount of energy is sensed. At 10-5 the sensed second parameter is calibrated against the preceding known pressure and the quantity of membrane deflection is determined. This, in turn, indicates flow. At 10-6 runs a self diagnosis to determines, among other things, whether the sensed flow is within a predetermined range, if not, then the device closes a valve and shuts down. Otherwise the device uses the new data to correct the sensed deflection against the known pressure and create a new baseline for future measurements.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A flow regulator, comprising:

a membrane having at least one hole;

a bottom layer comprising an outlet; and a fluid pathway;

the membrane being positioned above the bottom layer, the fluid pathway being defined from above the membrane through the hole and along the bottom layer on the side facing the membrane and through the outlet, wherein flow through the hole causes the membrane to deflect and engage against at least on portion of the bottom layer thereby impeding the fluid pathway by impeding flow through the hole in the membrane while not impeding flow through the outlet.

2. A flow regulator according to claim 1, wherein the side of the bottom layer facing the membrane further compromises at least one channel which constitutes a part of the fluid pathway, the first end of the channel being in connection with an outlet port, wherein flow through the hole causes the membrane to deflect and engage against at least one portion of the bottom layer thereby forcing the fluid in this portion to flow only in the channel.

3. A flow regulator according to claim 2, wherein the shape and length of the channel are so designed that an increase of pressure generates an increase of the contact area between the membrane and the bottom layer, thereby defining an additional segment to the channel where fluid is confined, said configuration allowing a proper adjustment of the flow versus pressure characteristics.

4. A flow regulator according to claim 3, wherein the section of the channel is constant.

5. A flow regulator according to claim 3, wherein the shape and length of the channel are so designed that the fluid resistance is proportional to the pressure, implying thereby a flow rate independent of the pressure.

6. A flow regulator according to claim 4 or 5, wherein the channel is spiral shaped groove.

7. A flow regulator according to any of claims 1 to 5, wherein the membrane further includes means for sensing the deflection of the membrane.

8. A flow regulator according to any of claims 1 to 5, wherein the fluid pathway is obstructed when the membrane has reached a predetermined degree of deflection.

9. A flow regulator, compromising:

a membrane having at least one hole;

a bottom layer; and a fluid pathway;

the membrane being positioned above the bottom layer, the fluid pathway being defined from above the membrane through the hole and along the bottom layer on the side facing the membrane, wherein flow thorough the hole causes the membrane to deflect and engage against at least one portion of the bottom layer there by impending the fluid pathway, wherein the side of the bottom layer facing the membrane further compromises at least one channel which constitutes a part of the fluid pathway, the first end of the channel being in connection with an outlet port, wherein flow through the hole causes the membrane to deflect and engage against at least one portion of the bottom layer thereby forcing the fluid in this portion to flow only in the channel, wherein the shape and length of the channel are so designed that an increase of pressure generates an increase of the contact area between the membrane and the bottom layer, thereby defining an additional segment of the channel where fluid is confined, said configuration allowing a proper adjustment of the flow versus pressure characteristics, wherein a section of the channel is constant and the channel is spiral shaped groove.

10. A flow regulator, compromising:

a membrane having at least one hole;

a bottom layer; and a fluid pathway;

the membrane being positioned above the bottom layer, the fluid pathway being defined from above the membrane through the hole and along the bottom layer on the side facing the membrane, wherein flow thorough the hole causes the membrane to deflect and engage against at least one portion of the bottom layer there by impending the fluid pathway, wherein the side of the bottom layer facing the membrane further compromises at least one channel which constitutes a part of the fluid pathway, the first end of the channel being in connection with in outlet port, wherein flow through the hole causes the membrane to deflect and engage against at least one portion of the bottom layer thereby forcing the fluid in this portion to flow only in the channel, wherein the shape and length of the channel are so designed that an increase generates an increase of the contact area between the membrane and the bottom layer, thereby defining an additional segment to the channel where fluid is confined, said configuration allowing a proper adjustment of the flow versus pressure characteristics, wherein the shape and length of the channel are so designed that the fluid resistance is proportional to the pressure, implying thereby a flow rate independent of the pressure and the channel is a spiral shaped groove.

* * * * *

UNITED STATES PATENT AND TRADEMARK OFFICE
CERTIFICATE OF CORRECTION

PATENT NO. : 6,878,135 B1
DATED : April 12, 2005
INVENTOR(S) : Haller et al.

It is certified that error appears in the above-identified patent and that said Letters Patent is hereby corrected as shown below:

<u>Column 6,</u>
Line 33, "least on portion" should be -- least one portion --.

<u>Column 8,</u>
Line 12, "with in outlet" should be -- with an outlet --.

Signed and Sealed this

Eighth Day of November, 2005

JON W. DUDAS
*Director of the United States Patent and Trademark Office*